United States Patent

Seto et al.

[11] Patent Number: 5,518,687
[45] Date of Patent: May 21, 1996

[54] DEVICE FOR TAKING OUT CHEMICAL ANALYSIS FILM CHIPS FROM A FILM CARTRIDGE

[75] Inventors: Yoshihiro Seto; Fumio Sugaya, both of Kanagawa; Yoshihiko Abe, Saitama; Yoshiyuki Doi, Kanagawa, all of Japan

[73] Assignee: Fuji Photo Film Co., Ltd., Kanagawa, Japan

[21] Appl. No.: 419,536

[22] Filed: Apr. 10, 1995

Related U.S. Application Data

[62] Division of Ser. No. 273,131, Jul. 14, 1994.

[30] Foreign Application Priority Data

Jul. 16, 1993 [JP] Japan .................................. 5-177055
Jul. 16, 1993 [JP] Japan .................................. 5-177057

[51] Int. Cl.⁶ .................................................. G01N 37/00
[52] U.S. Cl. ............................... 422/64; 422/63; 422/104; 436/43; 436/46; 436/48; 221/198; 221/226
[58] Field of Search ................................. 422/63, 64, 65, 422/66, 103, 104; 436/43, 46, 48; 221/279, 56, 198, 226

[56] References Cited

U.S. PATENT DOCUMENTS

| | | | |
|---|---|---|---|
| 3,848,962 | 11/1974 | Nelson | 350/86 |
| 3,992,158 | 11/1976 | Przybylowicz et al. | 23/253 |
| 4,151,931 | 5/1979 | Scherer et al. | 221/226 |
| 4,187,077 | 2/1980 | Covington et al. | 422/63 |
| 4,190,420 | 2/1980 | Covington et al. | 422/63 |
| 4,279,861 | 7/1981 | Jessop | 422/67 |
| 4,292,272 | 9/1981 | Kitajima et al. | 422/57 |
| 4,296,069 | 10/1981 | Smith et al. | 422/64 |
| 4,568,519 | 2/1986 | Hamilton et al. | 422/64 |
| 4,,855,109 | 8/1989 | Muraishi et al. | 422/63 |
| 4,876,204 | 10/1989 | Inoue et al. | 436/46 |
| 5,030,418 | 7/1991 | Miyata | 422/63 |
| 5,075,079 | 12/1991 | Kerr et al. | 422/64 |
| 5,154,889 | 10/1992 | Muraishi | 422/65 |
| 5,167,922 | 12/1992 | Long | 422/58 |
| 5,178,835 | 1/1993 | Uekusa et al. | 422/66 |

FOREIGN PATENT DOCUMENTS

| | | |
|---|---|---|
| 0064691 | 11/1982 | European Pat. Off. . |
| 0304838 | 3/1989 | European Pat. Off. . |
| 0397256 | 11/1990 | European Pat. Off. . |
| 0555654 | 8/1993 | European Pat. Off. . |
| 0567067 | 10/1993 | European Pat. Off. . |

*Primary Examiner*—Jill Warden
*Assistant Examiner*—Long V. Le
*Attorney, Agent, or Firm*—Sughrue, Mion, Zinn, Macpeak & Seas

[57] ABSTRACT

A chemical analysis film cartridge with a box-like casing body having first and second end walls opposed to each other between which a plurality of dry frameless chemical analysis film chips are stored in a stack. A first opening is formed in a side wall of the casing body near the first end wall so that only the film chip nearest the first end wall can be taken out of the casing body through the first opening by moving the film chip in a direction perpendicular to the stack. A second openings which permits a suction pad to hold the film chip nearest the first end wall and to remove it from the casing body through the first openings is formed in the first end wall. The width of the first opening is larger than the thickness of one film chip and smaller than double the thickness of one film chip over at least a portion of the first opening. The suction pad is retracted with the film chip so that the film chip abuts against the edge of the second opening on opposite sides of the suction pads and then the suction pad is further retracted to pull the central portion of the film chip in this state into the second opening, thereby reshaping the film chip into a predetermined warped-shape conforming to the shape of the first opening.

12 Claims, 11 Drawing Sheets

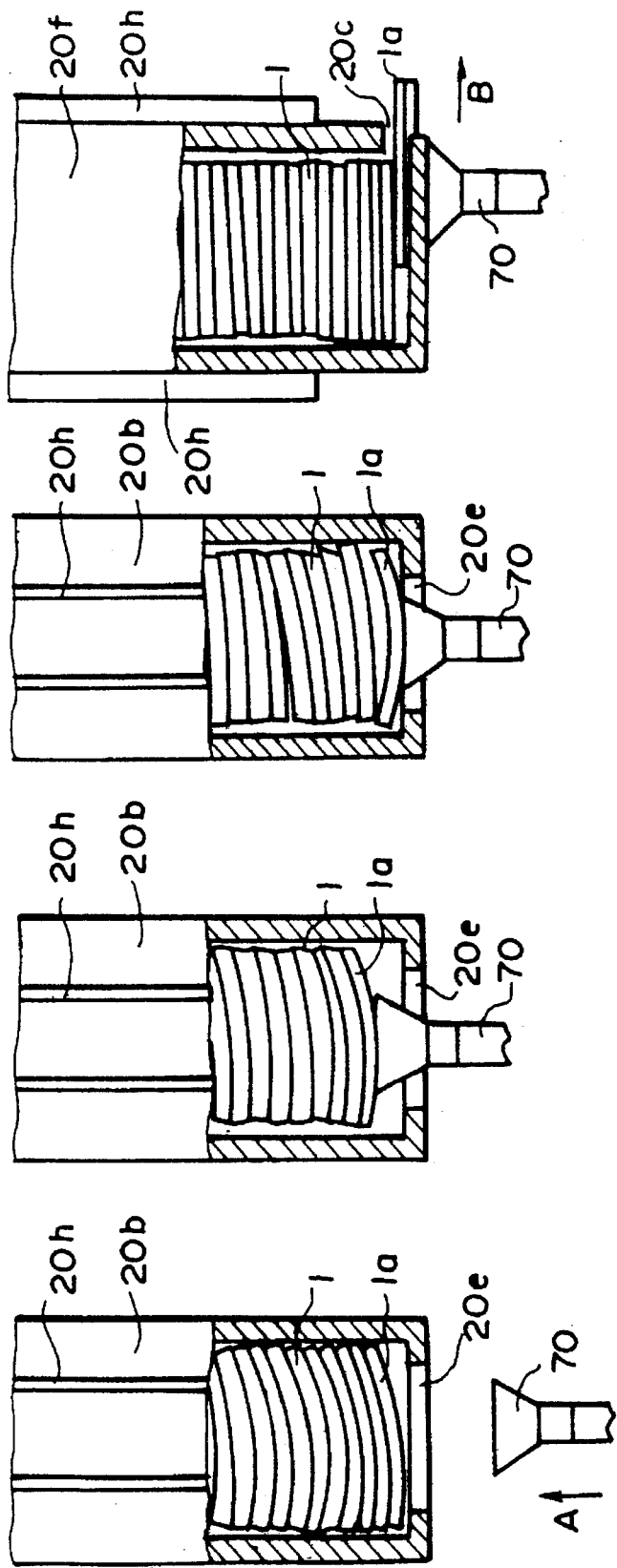

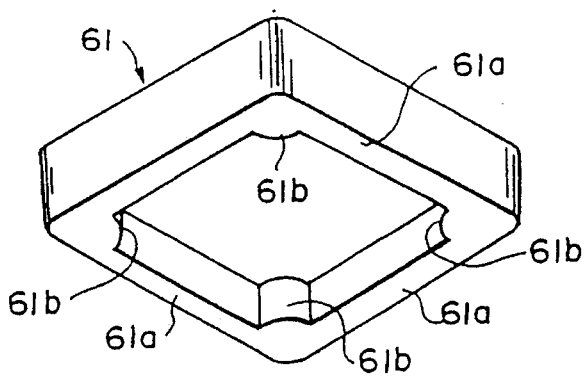
FIG.7
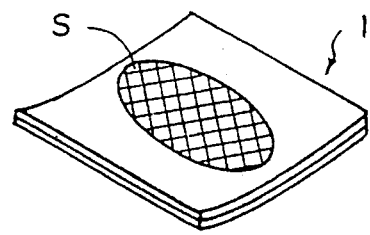
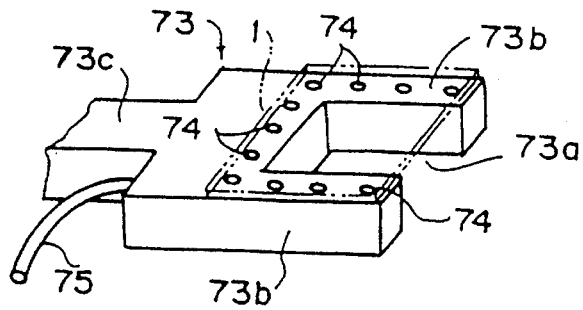
FIG.8
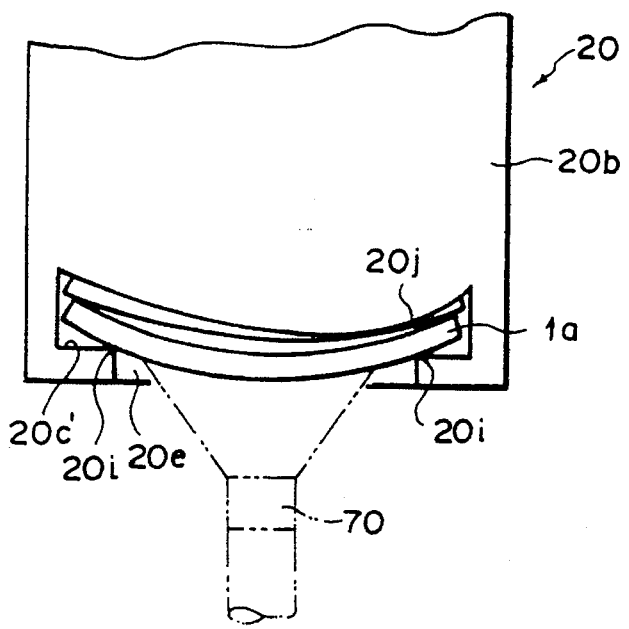
FIG.9

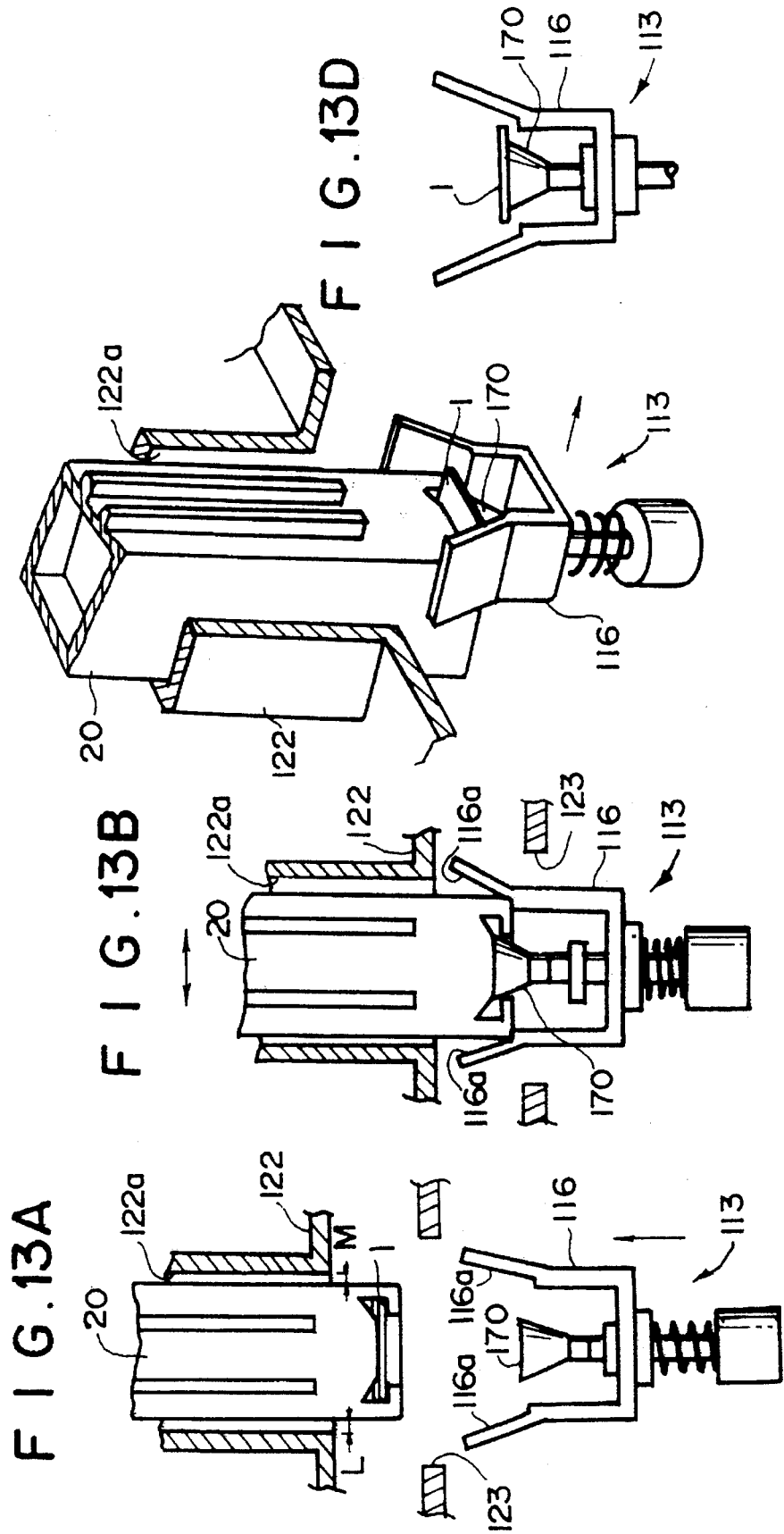

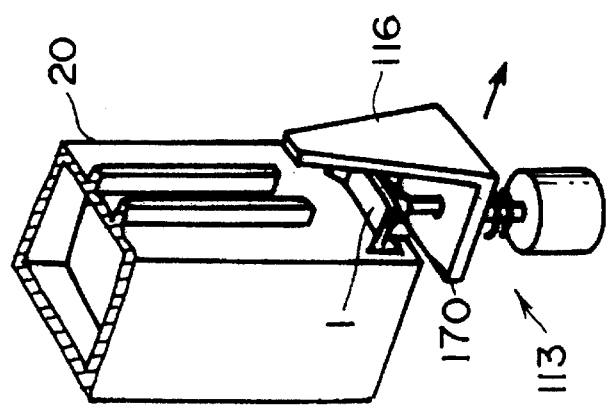
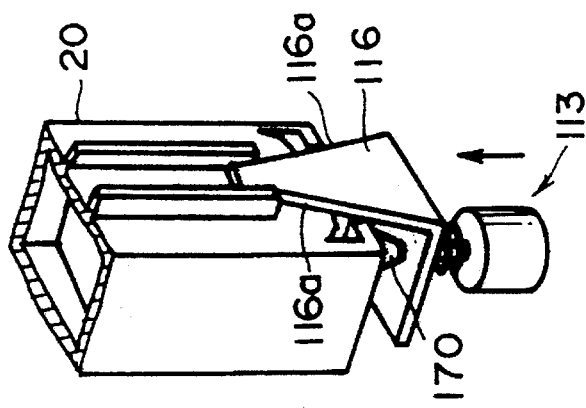
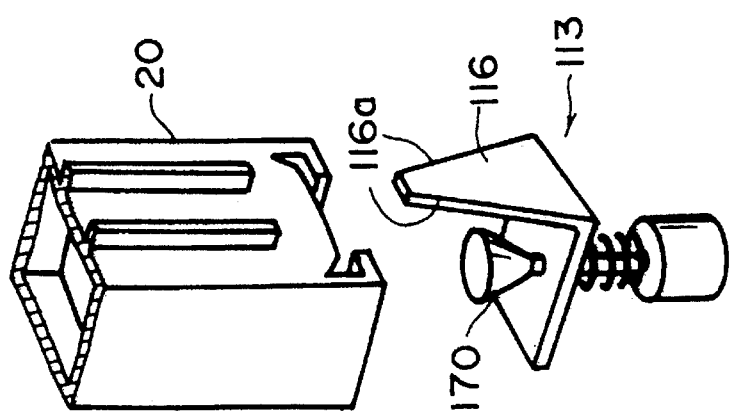

DEVICE FOR TAKING OUT CHEMICAL ANALYSIS FILM CHIPS FROM A FILM CARTRIDGE

This is a divisional of U.S. application No. 08/273,131, filed Jul. 14, 1994.

BACKGROUND OF THE INVENTION

1. Field of the Invention

This invention relates to a cartridge for storing a plurality of chemical analysis film chips each in a warped or curled state and having a reagent layer containing a reagent whose optical density changes through a chemical reaction, an immunoreaction or the like with a specific biochemical component contained in a sample liquid such as blood or urine. This invention further relates to a method of and a device for taking out the chemical analysis film chips from the cartridge one by one.

2. Description of the Prior Art

Quantitative or qualitative analysis of a specific component in a sample liquid is a common operation carried out various industrial fields. Especially, quantitative analysis of a chemical component or a solid component contained in a body fluid such as blood or urine is very important in the field of clinical biochemistry.

There has been put into practice a "dry-to-the-touch" chemical analysis slide with which a specific component contained in a sample liquid can be quantitatively analyzed through a droplet of the sample liquid applied to the slide by spotting. See Japanese Patent Publication No. 53(1978)-21677, U.S. Pat. No. 3,992,158, Japanese Unexamined Patent Publication No. 55(1980)-164356, U.S. Pat. No. 4,292,272 or the like. When such a dry chemical analysis slide is used, the sample liquid can be analyzed more easily and more quickly than when the conventional wet analysis method is used, and accordingly the dry chemical analysis slide is very convenient for medical facilities, laboratories and the like where lots of sample liquids have to be analyzed.

When chemical components or the like contained in a sample liquid is quantitatively analyzed using such a dry chemical analysis slide, a droplet of the sample liquid is applied to the slide and is held at a constant temperature for a predetermined time in an incubator so that coloring reaction occurs, and the optical density of the color formed by the coloring reaction is optically measured. That is, measuring light containing a wavelength which is preselected according to the combination of the component to be analyzed and the reagent contained in the reagent layer of the slide is projected onto the slide and the optical density of the slide is measured. Then the component to be analyzed is quantitatively analyzed on the basis of the optical density using a calibration curve, which represents the relation between the concentration of the biochemical component and the optical density.

The chemical analysis slide generally comprises a dry chemical analysis film chip and a plastic frame which holds the chemical analysis film chip flat to facilitate handling of the film chip during transfer. The chemical analysis film chip is generally composed of a support sheet of plastic or the like and a reagent layer and a spreading layer formed on the support sheet.

When biochemical analysis is effected using such chemical analysis slides, the chemical analysis slides should be smoothly supplied one by one in order to facilitate automated analysis.

There has been known a cartridge in which a stack of, for instance, about fifty chemical analysis slides are stored. See U.S. Pat. Nos. 4,151,931, 4,187,077, 4,190,420, 4,279,861 and the like.

In this cartridge, when the uppermost slide is pushed out of the cartridge by a push member, a lift member is inserted into the cartridge through the bottom of the cartridge to move upward the stack of the slides by a distance corresponding to the thickness of one slide. All the slides in the cartridge are taken out by repeating the steps.

Since a large number of the slides are consumed in a short time and accordingly a large cartridge is necessary, and moreover, there are required a plurality of cartridges the same as the biochemical substances to be analyzed in number, which results in increase in the size of the biochemical analysis apparatus.

Further, in the case of the chemical analysis slide, cost of the frame is high, which adds to cost of biochemical analysis.

Accordingly, we have proposed a dry chemical analysis element without frame. The chemical analysis element comprises a support sheet and a reagent layer and the like laminated on the support sheet and is not provided with a frame. This type of chemical analysis element will be referred to as "frameless chemical analysis film chip" or simply as "chemical analysis film chip", hereinbelow. Further we have proposed a cartridge for storing therein a stack of the frameless chemical analysis film chips. The cartridge has a box-like body which is provided with a first opening which is formed an upper portion of a side wall of the body and through which the uppermost chemical analysis film chip is only taken out and a second opening through which a means for holding the uppermost chemical analysis film chip and taking it out through the first opening is given access to the uppermost chemical analysis film chip. See Japanese Unexamined Patent Publication No. 4(1992)-5508 (corresponding to European Patent Publication No. 0555654A2).

The proposed cartridge for the frameless chemical analysis film chips can be substantially smaller than the conventional cartridge for the chemical analysis slides, whereby the overall size of the biochemical analysis apparatus can be miniaturized. Further the cost of the frame can be cut and the cost of biochemical analysis can be lowered.

However, use of the frameless chemical analysis film chip involves a problem that since the frameless chemical analysis film chips warp in a dry state, it is necessary to handle the chemical analysis film chips in an automated system taking into account the shape of the chemical analysis film chip in a dry state.

That is, though the reagent layer or reagent in a porous layer cannot initiate a reaction without water, it can initiate a reaction as soon as it absorbs water, which can adversely affect the result of the biochemical analysis. Accordingly, the chemical analysis film chips are stored in a dry atmosphere such as in a drying container (supplier) until they are to be applied with a sample liquid. In the dry state, the chemical analysis film chips are warped (curled or curved) into a roof tile-like shape, and the state (degree or shape) of warp substantially changes depending on the kind of the chemical analysis film chip, which is determined according to the item of measurement. Even if the kind of the chemical analysis film chips are the same, the state of warp can change from chip to chip.

Accordingly, the mechanism for taking out the chemical analysis film chips from the cartridge should be arranged so that the chemical analysis film chips in different states of warp can be surely taken out one by one.

In European Patent Publication No. 0064691A1, there is disclosed a technique for taking out from a container analytical elements for semi-quantitative analysis each comprising a reagent layer formed on a part of a support sheet. In the technique, a stack of the analytical elements is accommodated in the container, and the container is provided with an opening in the bottom thereof. A suction means is introduced into the container through the opening and attracts the lowermost element thereon under a suction force. Then the suction means is moved downward to pull out the element through the opening while resiliently deforming the element.

However when the technique is applied to the chemical analysis film chips, those having a small radius of curvature are apt to fall through the opening and when the opening is narrowed to prevent such chemical analysis film chips having a small radius of curvature from falling through the opening, then it becomes difficult to take out those having a large radius of curvature through the opening. Thus it is difficult to apply the technique to take out the chemical analysis film chips.

In Japanese Unexamined Patent Publication No. 4(1992)-16098 (corresponding to European Patent Publication No. 0555654A2), there is further disclosed a supplier for storing a plurality of frameless chemical analysis film chips in a dry state before application of sample liquid. The supplier is provided with a cartridge holding means for holding a plurality of cartridges and the cartridge holding means is driven by a drive mechanism such as an electric motor to bring a desired cartridge to a film takeout port formed in the supplier. A suction means is provided near the film takeout port and takes out the film chip from the cartridge positioned opposed to the film takeout port. That is, the suction means is movable between a predetermined attracting position and a retracted position away from the attracting position. The attracting position is where the suction means can precisely attract the center of the film chip in the cartridge opposed to the film takeout port under a suction force. The suction means is moved to the attracting position from the retracted position after a desired cartridge is moved to the position opposed to the film takeout portion and takes out the film chip while holding it under a suction force.

It is important that the cartridge is in a fixed position relative to the attracting position when it is positioned opposed to the film takeout port (this position will be referred to as "the film takeout position" hereinbelow) since otherwise the suction means cannot attract the film chip at a constant portion. If the portion at which the suction means attracts the film chip changes chip to chip, various troubles can be caused during subsequent handling of the film chip. For example, the sample liquid cannot be applied to the film chips in a constant position therein, or the film chip can be brought into contact with a wall of a cell in an incubator when it is inserted into the cell and the sample liquid on the film chip can contaminate the cell or the film chip can be broken on impact.

Though there have been made various attempts to precisely position the cartridge in the film takeout position relative to the attracting position by improving the precision of the cartridge holding means drive mechanism, it has been difficult to improve the precision of the cartridge holding means drive mechanism to such a level. Especially when the cartridge holding means is in the form of a cartridge receiving portion which is formed in a disk-like rotary body and is moved along a circular path unlike that disclosed in Japanese Unexamined Patent Publication No. 4(1992)-16098 (corresponding to European Patent Publication No. 0555654A2) where the cartridge holding means is moved along a linear path, it is very difficult to precisely position the cartridge in the circumferential direction of the rotary body though the cartridge can be substantially precisely positioned in the radial direction of the rotary body.

SUMMARY OF THE INVENTION

In view of the foregoing observations and description, the primary object of the present invention is to provide a cartridge for storing a plurality of chemical analysis film chips in a stack which cartridge permits the chemical analysis film chips to be surely taken out one by one irrespective of their states of warp.

When the cartridge with a number of chemical analysis film chips stacked therein is transferred, it is preferred that the chemical analysis film chips be prevented from falling from the cartridge through a film takeout port when an impact is applied to the cartridge.

Thus another object of the present invention is to provide a cartridge for storing a plurality of chemical analysis film chips in a stack which cartridge permits the chemical analysis film chips to be surely taken out one by one irrespective of their states of warp while preventing the chemical analysis film chips from falling from the cartridge when an impact is applied to the cartridge.

Still another object of the present invention is to provide a method of surely taking out the chemical analysis film chips one by one from the cartridge irrespective of their states of warp while preventing the chemical analysis film chips from falling from the cartridge when the chemical analysis film chips are not used.

Still another object of the present invention is to provide a method of and a device for precisely positioning a cartridge with respect to a suction means (a film takeout means) so that the suction means can precisely attract a predetermined portion of the film chip.

The cartridge of the present invention comprises a box-like casing body which has first and second end walls opposed to each other and in which a plurality of dry frameless chemical analysis film chips, each having a reagent containing layer formed on a support sheet, are stored in a stack extending between the end walls. A first opening is formed in a side wall of the casing body at a portion near to the first end wall of the casing body so that only the chemical analysis film chip nearest to the first end wall in the chemical analysis film chips in the stack can be taken out of the casing body through the first opening by moving the chemical analysis film chip in the direction perpendicular to the direction of the stack. A second opening which permits a film takeout means to hold the chemical analysis film chip nearest to the first end wall and take it out of the casing body through the first opening is formed in the first end wall of the casing body. The cartridge of the present invention is characterized in that the width of the first opening is larger than the thickness of one chemical analysis film chip and smaller than double the thickness of one chemical analysis film chip at least a part of the first opening.

In one embodiment of the present invention, an urging means for urging the stack of the chemical analysis film chips toward the first end wall is provided in the casing body.

In another embodiment of the present invention, the first opening is provided with a projection which prevents the chemical analysis film chip nearest to the first end wall from going out the casing body through the first opening when the film chip is in the normal state.

The method of taking out the chemical analysis film chips in accordance with the present invention is for taking out a plurality of dry frameless chemical analysis film chips, each having a reagent containing layer formed on a support sheet, one by one from a cartridge comprising a box-like casing body which has first and second end walls opposed to each other and in which the chemical analysis film chips are stored in a stack extending between the end walls, a first opening being formed in a side wall of the casing body at a portion near to the first end wall of the casing body so that only the chemical analysis film chip nearest to the first end wall in the chemical analysis film chips in the stack can be taken out of the casing body through the first opening by moving the chemical analysis film chip in the direction perpendicular to the direction of the stack and a second opening being formed in the first end wall of the casing body so that a film takeout means can hold the chemical analysis film chip nearest to the first end wall through the second opening and take the film chip out of the casing body through the first opening.

The method of the present invention is characterized by the steps of inserting a film takeout means into the casing body through the second opening and causing the film takeout means to attract and hold the chemical analysis film chip nearest to the first end wall under a suction force, retracting the film takeout means toward the second opening by a predetermined distance with the film chip held on the film takeout means to bring opposite side portions of the film chip held on the film takeout means into abutment against the inner edge of the second opening and further moving the film takeout means in the same direction, thereby reshaping the film chip into a predetermined warped-shape which is convex outward from the second opening, and moving the film takeout means toward the first opening with the film chip held in the warped state to carry the film chip out of the casing body through the first opening which is formed in the predetermined warped-shape.

The term "the width of the first opening" means the space between the edges of the first opening opposed to each other in the direction of the stack of the chemical analysis film chips.

The term "the film chip is in the normal state" means that the film chip is simply in the stack free from the film takeout means.

The projection for preventing the chemical analysis film chip nearest to the first end wall from going out the casing body through the first opening has an edge portion which can prevent a film chip having the smallest radius of curvature from passing through the first opening when it is in the normal state but permits any film chip reshaped into the predetermined warped-shape to pass through the first opening without interference with the projection. Though the chemical analysis film chip can be in complicatedly warped or curved state, the radius of curvature as used in this specification means that of the primary warp or curve of the film chip as viewed in the direction of movement of the film chip when it is passed through the first opening by the film takeout means.

In the reshaped state, each film chip has a radius of curvature smaller than that of the film chip having the smallest radius of curvature in the normal state.

In the cartridge of the present invention, since the width of the first opening is larger than the thickness of one chemical analysis film chip and smaller than double the thickness of one chemical analysis film chip at least a part of the first opening, when the film chip nearest to the second opening (will be referred to as "the leading film chip", hereinbelow) is reshaped as described above and moved through the first opening by the film takeout means, the film chips other than the leading film chip which can move toward the first opening trailed by the leading film chip are stopped by the side wall of the casing body and accordingly only the leading film chip can be passed through the first opening.

When an urging means for urging the stack of the chemical analysis film chips toward the first end wall is provided in the casing body, the leading film chip can be constantly positioned near the first end wall irrespective of the number of the film chips in the cartridge, whereby the stroke of the film takeout means by which the film takeout means is inserted into the casing body to hold the leading film chip can be uniform irrespective of the number of the film chips in the cartridge and automated operation of taking out the film chip can be smoothly effected.

Further when the first opening is provided with a projection which prevents the chemical analysis film chip nearest to the first end wall from going out the casing body through the first opening when the film chip is in the normal state, the chemical analysis film chips are prevented from falling from the cartridge when an impact is applied to the cartridge from outside the cartridge, for instance, during transfer.

In the method of taking out the film chip from the cartridge in accordance with the present invention, the suction means is retracted with the film chip held on the suction means so that the film chip held on the suction means abuts against the edge of the second opening on opposite sides of the suction means and then further retracted to pull the central portion of the film chip in this state into the second opening, thereby reshaping the film chip into a predetermined warped-shape.

Thus each of the chemical analysis film chips in various warped-shapes is once reshaped into the predetermined warped-shape which substantially conforms to the shape of the first opening by pulling the central portion of the film chip into the second opening while supporting the opposite side portions of the film chip by the inner surface of the first end wall on opposite sides of the second opening.

Then the film chip is passed through the first opening being kept in the predetermined warped-shape.

Accordingly when the leading film chip is taken out, the film chips other than the leading film chip which can move toward the first opening trailed by the leading film chip by a friction force therebetween are stopped by the side wall of the casing body and accordingly only the leading film chip can be passed through the first opening.

The first opening has a radius of curvature smaller than that of the film chip having the smallest radius of curvature in the normal state, and accordingly the chemical analysis film chips cannot fall from the cartridge through the first opening even when an impact is applied to the cartridge from outside the cartridge, for instance, during transfer.

By arranging the film takeout means to attract the support sheet of the film chip under a suction force when taking out the film chip from the cartridge, the reagent layer and/or the spreading layer of the film chip are not subjected to a force and can be prevented from being damaged.

The method of positioning a cartridge with respect to a film takeout means in accordance with the present invention is for positioning a cartridge with respect to a film takeout means in the form of a suction means when a frameless chemical analysis film chip is to be taken out from the cartridge held by a cartridge holding means by attracting the chemical analysis film chip under a suction force by the suction means in a predetermined attracting position, and is characterized in that the cartridge is held by the cartridge holding means with a predetermined play, and the cartridge is guided to a predetermined conforming position within the range of the predetermined play when the film chip is taken out from the cartridge.

The "predetermined attracting position" is a predetermined fixed position where the suction means is to be positioned when it attracts the chemical analysis film chip in the cartridge to take it out from the cartridge.

The "predetermined conforming position" is a position where the cartridge is to be positioned with respect to the cartridge in order to permit the suction means to precisely attract a predetermined portion of the film chip.

The device for positioning a cartridge with respect to a film takeout means in accordance with the present invention is for positioning a cartridge with respect to a film takeout means in the form of a suction means when a frameless chemical analysis film chip is to be taken out from the cartridge held by a cartridge holding means by attracting the chemical analysis film chip under a suction force by the suction means in a predetermined attracting position, and is characterized in that the cartridge holding means is arranged to hold the cartridge with a predetermined play, and there is provided a guide means which is adapted to engage with the cartridge held by the cartridge holding means to guide the same within the predetermined play in the vicinity of the suction means to a predetermined conforming position, said predetermined conforming position being a position where the cartridge is to be positioned with respect to the suction means in order to permit the suction means to precisely attract a predetermined portion of the film chip.

It is preferred that the guide means guides the cartridge to the conforming position in response to movement of the suction means to the attracting position.

For example, the guide means may be in the form of a guide member which is formed at least one of the cartridge and the suction means and is caused to slide on the other to guide the cartridge to the conforming position while the suction means is moving toward the cartridge to the attracting position.

In the method and the device of the present invention, the position of the cartridge held by the cartridge holding means is adjusted within the play with respect to the suction means and the cartridge can be positioned precisely in the conforming position with respect to the attracting position, whereby the suction means can precisely attract a predetermined portion of the film chip.

In accordance with the present invention, by deliberately providing a play between the cartridge and the cartridge holding means, the error in precision of the cartridge holding means drive mechanism can be compensated for and the cartridge can be precisely positioned in the conforming position by adjusting the position of the cartridge with respect to the attracting position or the suction means within the play. Thus the suction means can precisely attract a predetermined portion of the film chip, which ensures better biochemical analysis.

BRIEF DESCRIPTION OF THE DRAWINGS

FIGS. 5A to 5D are schematic views for illustrating the procedure of taking out the film chip from the cartridge, FIG. 7 is a schematic perspective view showing the film retainer in the cell of the incubator, FIG. 8 is a perspective view showing the transfer member shown in FIG. 6, FIG. 9 is a schematic view showing a modification of the first opening, FIGS. 13A to 13D are views showing the procedure for positioning the cartridge with respect to the suction means by the film takeout device shown in FIG. 12, FIGS. 14A to 14C are views showing the procedure for positioning the cartridge with respect to the suction means by a modification of the film takeout device shown in FIG. 12, FIGS. 15A and 15B are perspective views showing a modification of the film takeout device shown in FIG. 10.

DESCRIPTION OF THE PREFERRED EMBODIMENT

Figure 1A:
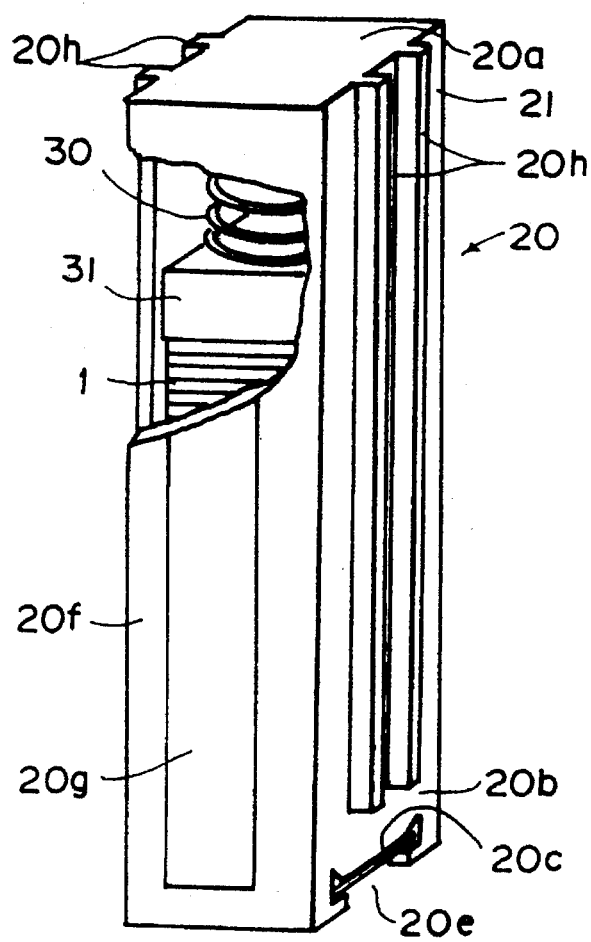
FIG. 1A is a perspective view partly cut away showing a chemical analysis film chip cartridge in accordance with an embodiment of the present invention.
Figure 1B:
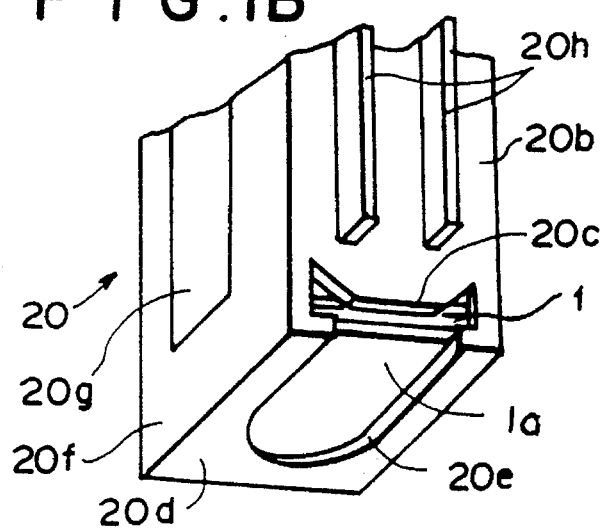
FIG. 1B is a fragmentary perspective showing a bottom portion of the cartridge.

FIG. 1A is a perspective view partly cut away showing a cartridge 20 in accordance with an embodiment of the present invention and FIG. 1B is a fragmentary perspective view showing the bottom of the cartridge 20. The cartridge 20 comprises a box-like casing 21 for accommodating a stack of chemical analysis film chips 1, a spring member 30 mounted on the inner side of the top wall 20a of the casing 21 and a pushing member 31 which is mounted on the lower end portion of the spring member 30 and urges downward the stack of the film chips 1. A first opening 20c is formed in one side wall 20b of the casing 21 at a portion near to the bottom wall 20d of the casing 21. The first opening 20c is shaped and sized to permit only the lowermost film chip of the stack to pass therethrough. A U-shaped second opening 20e which gives a suction pad 70 (FIG. 4) for holding the film chip 1 access to the lowermost film chip 1a is formed in the bottom wall 20d of the casing 21. A part of the side wall 20b below the first opening 20c is cut away so that the first opening 20c and the second opening 20e communicate with each other.

On the outer surface of another side wall 20f of the casing 21, there is recorded magnetic stripes (or a magnetic band) 20g which carries information such as properties of the film chips 1 accommodated in the cartridge 20. A pair of ribs 20h are formed in each of the side wall 20b and the side wall opposite to the side wall 20b in order to hold the cartridge 20 in a cartridge holding portion 22a (to be described later with reference to FIG. 6) and to prevent insertion of the cartridge 20 in a wrong position.

The bottom wall 20d of the casing 21 is removable from the side walls of the casing 21 and is inserted into the side walls with the stack of the film chips 1 placed thereon so that the uppermost film chip is pressed against the pushing member 31, whereby the lower film chip 1a is pressed against the inner surface of the bottom wall 20d under the force of the spring member 30. The bottom wall 20d is fixed there by a suitable means (not shown).

The casing 21 is, for instance, 15 mm×15 mm×100 mm in size and about 1 mm in wall thickness. The casing 21 may be formed of light-shielding black plastic material such as polystyrene.

Information on the film chips 1 in the cartridge such as those representing the kind of the film chips 1, lot correction information, the items of analysis, the number of the film chips and the like are magnetically recorded on the magnetic stripes 20g, and a magnetic head in the analysis system reads the information for the subsequent biochemical analysis.

Figure 2A:
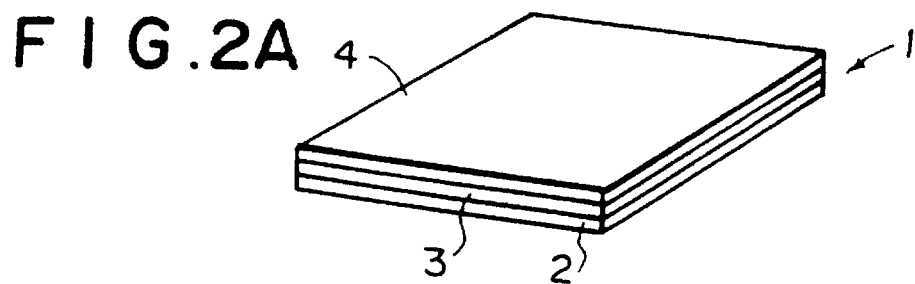
FIG. 2A is a perspective view showing a chemical analysis film chip under the normal humidity condition.
Figure 2B:
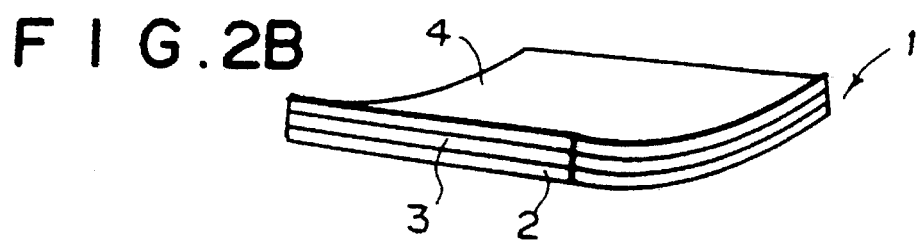
FIGS. 2B and 2C are perspective views showing the chemical analysis film chip in a dry state.
Figure 2C:
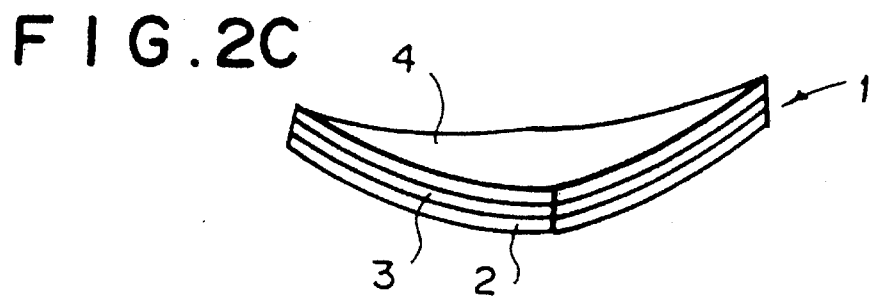

FIG. 2A shows the chemical analysis film chip 1 and FIGS. 2B and 2C show the state of the chemical analysis film chip 1 in a dry state.

The film chip 1 is formed by coating or bonding a reagent layer 3 on a transparent support sheet 2 of an organic polymer sheet or the like (e.g., polyethylene terephthalate sheet or polystyrene sheet), and laminating a spreading layer 4 on the reagent layer 3. It should be noted that the film chip 1 is not provided with any frame.

The reagent layer 3 comprises at least one layer composed of a porous layer or a hydrophilic polymer binder such as gelatin containing therein a reagent component which makes coloring reaction with analyte.

The spreading layer 4 is formed of woven or knitted fabric (or cloth) of synthetic fiber resistant to rubbing such as polyester, or of blend of natural fiber and synthetic fiber, unwoven fabric or paper and functions as a protective layer. Further the spreading layer 4 causes sample liquid applied thereto to uniformly spread over the reagent layer 3.

The thickness of the support sheet 2 is, for instance 150 to 200 μm, the thickness of the reagent layer 3 is, for instance 10 to 40 μm, and the thickness of the spreading layer 4 is, for instance 200 to 250 μm.

The support sheet 2, the reagent layer 3 and the spreading layer 4 are of substantially the same size and for instance 12 mm×12 mm.

Under the normal humidity conditions the film chip 1 is substantially flat as shown in FIG. 2A. The film chip 1 is stored in a dry environment (e.g., in an environment where the humidity is not higher than 20%) in order to suppress chemical reaction, and in a dry state, the film chip 1 is warped (curled or curved) toward the spreading layer 4 as shown in FIG. 2B or 2C. In the state shown in FIG. 2B, the film chip 1 is curled in one direction and in the state shown in FIG. 2C, the film chip 1 is curled in a plurality of directions.

The direction of curl and the curvature thereof varies depending on the kind of the reagent in the reagent layer 3, the arrangement of the layers and the kind of material of the support sheet 2. For example, when a film chip 1 which is 12 mm×12 mm in size and 0.5 mm in thickness is stored in an absolute dry state for five days, the curvature is about 100 to 1500 μm at the maximum.

A plurality of (e.g., 100 pieces) film chips 1 are stacked with the support sheet 2 facing downward and set between the pushing member 31 and the bottom wall 20d of the casing 21.

Figure 3A:
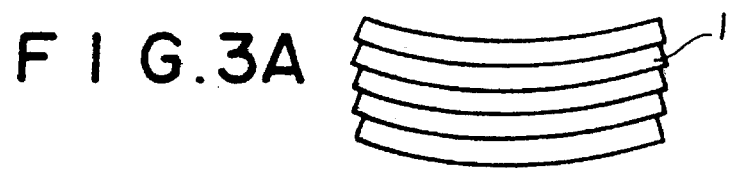
FIGS. 3A and 3B are schematic views showing the stack of the chemical analysis film chips in the cartridge.
Figure 3B:

Since the film chips 1 are curled toward the spreading layer 4 in the dry state, they are stacked in the cartridge 20 in a state as shown in FIG. 3A or 3B.

It is difficult for the conventional automatic chemical analysis system as it is to handle the curled film chip 1. That is, operation of taking out the film chips 1 one by one from a cartridge in a drying container (supplier), operation of applying sample liquid to the film chip 1 and transferring it to an incubator, operation of inserting the film chip 1 into a cell of the incubator and incubating it at a constant temperature and operation of measuring the optical density after a predetermined time and taking out and discarding the film chip 1 all must be carried out taking into account the shape of the film chip 1. The first opening 20c of the cartridge 20 described above is shaped taking into account the shape of the film chip 1.

Figure 4A:
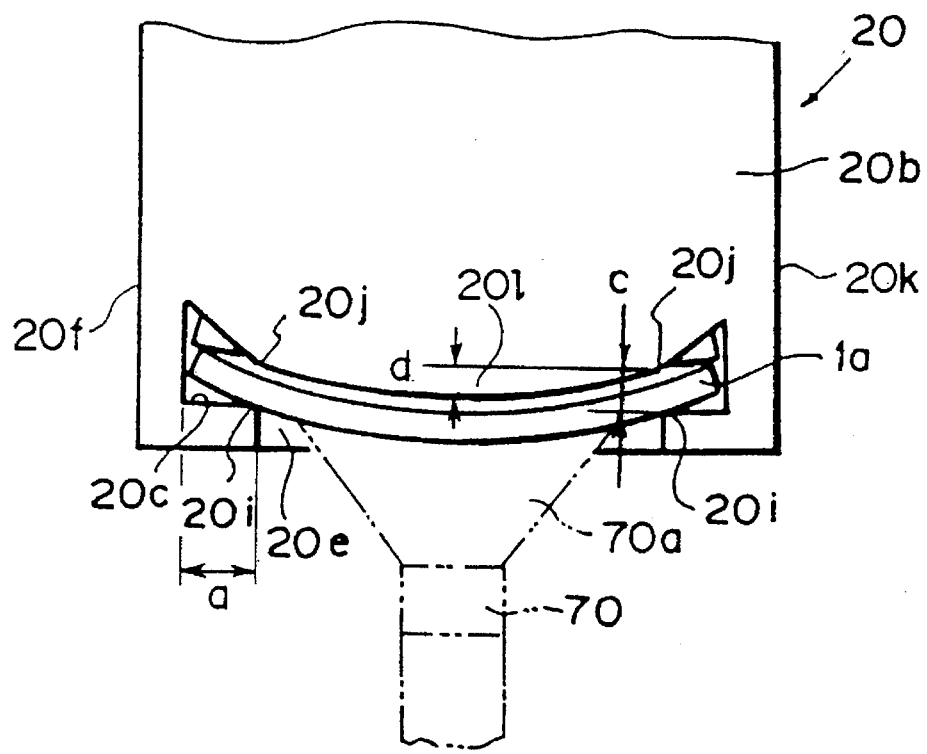
FIGS. 4A and 4B are schematic views for illustrating the shape of the first opening of the cartridge.

As shown in FIG. 4A, the first opening 20c is sized and shaped so that the film chip 1a can be passed through the first opening 20c so long as it has been reshaped into a predetermined warped-shape in the manner to be described later. However, even if the respective film chips are reshaped, the warped-shape somewhat differs from chip to chip, and accordingly, only the space c between each of the edges 20i of the second opening 20e and the upper edge of 20j of the first opening 20c just above the edge 20i is strictly set to a value larger than the thickness of one film chip 1 and smaller than double the thickness of the same, and the first opening 20c is somewhat wider than the space c at the other parts so that the film chips 1 can be surely and smoothly taken out through the first opening 20c irrespective of minor differences in shape of the film chips in the reshaped state.

More particularly, the width (the space between the upper and lower edges) of first opening 20c is gradually enlarged toward the respective ends.

When the length a of the margin of the bottom wall 20d which supports opposite edge portions of the film chip 1a, i.e., the distance between the edge 20i of the second opening 20e and the inner surface of the side wall 20f or 20k, is short, the film chip 1a can be reshaped with a relatively weak force. However when the length a is too short, there is fear that the film chip 1a falls through the second opening 20e when an impact is applied to the cartridge. Accordingly, it is preferred that the length a be set as short as possible so long as it does not cause the fear. For example, the length a may be 1 mm.

Figure 4B:
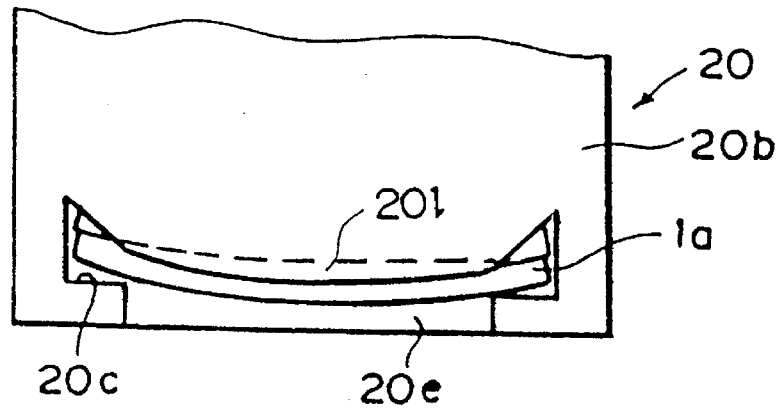

A protrusion 201 is provided on the central portion of the upper edge of the first opening 20c. The protrusion 201 prevents the other film chips 1 from passing through the first opening 20c when the lowermost film chip 1a is passed therethrough and at the same time prevents the lowermost film chip 1a from passing through the first opening 20c in case that an impact is applied to the cartridge 20 in the normal state of the lowermost film chip 1a where it is not reshaped by the suction pad 70. Accordingly the extreme portion of the protrusion extends beyond the upper edges 20j of the first opening 20c by a distance d which ensures that even the film chip 1 having the smallest radius of curvature in the normal state interferes with the inner surface of the protrusion 201 as shown in FIG. 4B unless it is reshaped, e.g., when the film chips 1 are stored.

It is needless to say that the distance d and the curvature of the lower edge of the protrusion 201 should be set to permit the lowermost film chip 1a to pass through the first opening 20c when it is held by the suction pad 70 and reshaped into the predetermined warped-shape.

How to take out the film chips 1 from the cartridge will be described with reference to FIGS. 5A to 5D, hereinbelow.

As shown in FIG. 5A, the film chips 1 are stacked in the cartridge 20 with each of the film chips 1 curled to be convex downward and the stack is pressed against the upper surface of the bottom wall 20d under the force of the spring member 30. The spring force of the spring member 30 is set so that, even after all the film chips 1 but one are taken out from the cartridge 20, the spring member 30 can press the last film chip 1 against the upper surface of the bottom wall 20d.

The suction pad 70 for taking out the film chip 1 is positioned below the second opening 20e of the casing 21 and is moved upward (in the direction of arrow A) under the control of a controller.

The suction pad 70 is inserted through the second opening 20e to be brought into abutment against the lowermost film chip 1a and further moved upward into closer contact with the lowermost film chip 1a as shown in FIG. 5B. In this position, the suction pad 70 holds the lowermost film chip 1 under a suction force supplied from a vacuum pump not shown. Since the suction pad 70 attracts the support sheet 2 of the film chip 1a, the film chip 1a can be surely attracted on the suction pad 70 under the suction force and there is no possibility of damaging the reagent layer 3 and/or spreading layer 4.

The support sheet 2 is arranged to be strong enough to withstand the suction force acting on the film chip 1 during taking out from the cartridge 20 and during subsequent transfer thereof.

Thereafter the suction pad 70 is moved downward holding the film chip 1a under the control of the controller until the film chip 1a is reshaped into the predetermined warped-shape convex downward as shown in FIG. 5C. That is, the parts of the film chip 1a on opposite sides of the suction pad 70 is brought into abutment against the edges of the second opening 20e on the way, and as the suction pad 70 is further moved downward, the central portion of the film chip 1a is pulled downward with the parts of the film chip 1a on opposite sides of the suction pad 70 supported by the edges of the second opening 20e, whereby the film chip 1a is reshaped into the predetermined warped-shape.

The total suction force applied to the support sheet 2 during the reshaping is set to, for instance, not smaller than 300 g assuming that the film chip 1a is 12 mm× 12 mm in size and the maximum diameter of a suction cup 70a of the suction pad 70 is 9 mm. The force to be applied to the suction pad 70 to pull the film chip 1a during the reshaping should be sufficiently smaller than the suction force, e.g., 100 g, in order to prevent the film chip 1a from being released from the suction pad 70 or being moved relative to the suction pad 70 during the reshaping.

The reason why the film chip 1a is reshaped into the predetermined warped-shape is that the film chips 1 in the cartridge 20 are warped or curled in different curvatures and in different shapes and since the first opening 20c is shaped and sized to permit only one film chip 1 to pass therethrough, the film chip 1 cannot be passed through the first opening 20c unless its shape and curvature conform to the shape of the first opening 20c.

After the reshaping, the suction pad 70 is moved in the direction of arrow B holding the reshaped film chip 1a to take out the same through the first opening 20c as shown in FIG. 5D.

Since the film chip 1a is reshaped into the predetermined warped-shape, the support sheet 2 is formed not to be damaged (cracked) when it is warped while it is attracted by the suction pad 70.

Further, when the lowermost film chip 1a is taken out, the spreading layer 4 of the lowermost film chip 1 is rubbed with the support sheet 2 of the second lowermost film chip 1, and accordingly it is preferred that the friction coefficient between the spreading layer 4 and the support sheet 2 be small (e.g., not larger than 1) so that the lowermost film chip 1a can be smoothly taken out.

After the lowermost film chip 1a is taken out, the stack of the film chips 1 are moved downward under the force of the spring member 30 by the distance corresponding to the thickness of the film chip 1.

An automated biochemical analysis apparatus for effecting biochemical analysis using the chemical analysis film chip 1 taken out from the cartridge will be described hereinbelow.

Figure 6:
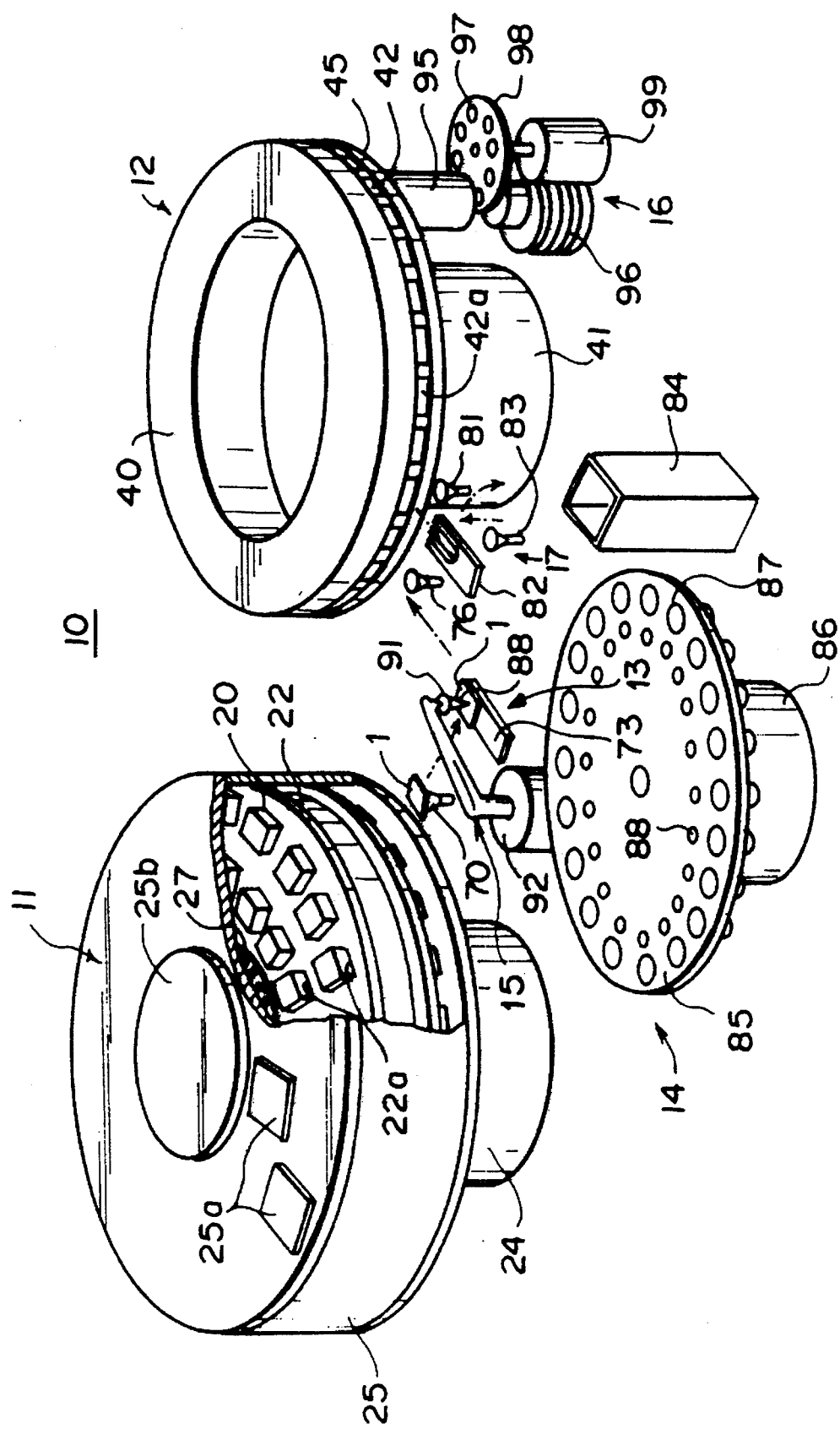
FIG. 6 is a schematic perspective view showing an biochemical analysis apparatus for effecting biochemical analysis using the chemical analysis film chip shown in FIG. 2.

FIG. 6 is a perspective view showing an example of such a biochemical analysis apparatus.

The biochemical analysis apparatus 10 comprises a film supplier 11 in which a plurality of virgin film chips 1 are stored, an incubator 12 which is disposed beside the film supplier 11 and incubates the film chips 1 transferred from the film supplier 11, a film transfer means 13 which transfers the film chips 1 from the film supplier 11 to the incubator 12, a sample liquid supplier 14 in which a plurality of sample liquids such as serum, urine or the like are stored, a spotting mans 15 which applies one of the sample liquids in the sample liquid supplier 14 to the film chips 1 on the way to the incubator 12, and a light measuring system 16 disposed below the incubator 12.

The film chips 1 are stored in cartridges 20 for the respective items of analysis. In the cartridge 20, a plurality of the film chips 1 are stacked with the support sheet 2 facing downward. As shown in FIG. 6, the film supplier 11 is provided with a plurality of cartridge holding portions 22a which are arranged in inner and outer circles on a disk-like support 22 and a plurality of cartridges 20 loaded with the film chips 1 are held in the respective cartridge holding portions 22a. The support 22 is supported for rotation on a base portion 24 and is rotated by a motor not shown so that a predetermined cartridge holding portion 22a is brought to a film takeout position where the film transfer means 13 takes out a film chip 1 from the cartridge 20.

The support 22 is provided with a cover 25 which encloses the inner space of the film supplier 11. The cover 25 is provided with a pair of openings 25a provided with lids and the cartridges 20 can be taken out and inserted into the cartridge holding portion 22a through the openings 25a. An dehumidifying agent holding portion 27 is formed in the support 22 at the center thereof and dehumidifying agent (dessicant) is loaded in the dehumidifying agent holding portion 27 through an opening 25b formed in the cover 25. The opening 25b is provided with a lid. Thus the inner space of the film supplier 11 is kept dry. A shutter (not shown) is provided in the lower surface of the cover 25 in the film takeout position. The shutter is opened when the film chip 1 is taken out from the cartridge 20 and a suction pad 70 of the film transfer means 13 takes out the lowermost film 1 in the cartridge 20 through the shutter.

As shown in FIG. 6, the incubator 12 comprises a disk-like body portion 40 which is supported to be rotated by a drive mechanism 41 disposed below the body portion 40 at the center thereof. A plurality of cells 42 are provided in the body portion 40 at predetermined intervals in the circumferential direction thereof. The film chips 1 are incubated in the cells 42.

The body portion 40 comprises a lower disk 45 of metal having a flat upper surface and an upper disk of metal (not shown) provided on the lower disk 45 and is fixed to the lower disk 45 by screws. The peripheral edge portion of the upper disk is bulged upward to form an annular channel open downward. The lower edge of the outer peripheral edge of the upper disk is spaced from the upper surface of the lower disk 45 to form an opening which opens in the side surface of the incubator 12 and gives access to the cells 42. A heater (not shown) is disposed between the lower and upper disks. The heater is controlled to heat the film chips 1 in the cells 42 to a predetermined temperature (e.g., 37° C.) on the basis of the output of a temperature sensor (not shown).

A plurality of light measuring windows for photometry are formed in the lower disk 45 to be opposed to the respective cells 42, and a film retainer (or cover) 61 (FIG. 7) for fixing the film chip 1 in a predetermined position in the cell 42 is provided above each of the light measuring windows. A measuring system 16 has a light measuring head 95 which is disposed below the body portion 40 in a light measuring position.

As shown in FIG. 7, the film retainer 61 has a rectangular frame portion 61a on the lower surface thereof. The inner dimensions of the frame portion 61a is larger than the outer dimensions of the film chip 1 and a protrusion 61b is provided at each corner of the frame portion 61a to project inward. When the film retainer 61 is moved downward against the film chip 1, only the protrusions 61b are brought into contact with the film chip 1 so that the retainer 61 is not brought into contact with the portion S over which the sample liquid can spread. The film retainer 61 is urged downward under the force of a spring provided on the upper surface of the retainer 61.

Thus the film chip 1 is kept flat during incubation and measurement of the optical density, whereby incubation can be effected with a high efficiency and the accuracy of analysis can be ensured.

The film transfer means 13 for transferring the film chip 1 from the film supplier 11 to the incubator 12 comprises said suction pad 70 for taking out the film chip 1 from the cartridge 20, a horseshoe-like transfer member 73 which receives the film chip 1 held on the suction pad 70 from below the film chip 1 with the reagent layer 3 facing upward and inserts the film chip 1 into the cell 42 in the incubator 12 through the opening which opens sideways, and a suction member 76 which moves in and out the cell 42 from below the cell and receives the film chip 1 held by the transfer member 73 inside the cell 42.

The suction pad 70 comprises a suction cup 70a which is directed upward and attracts the lower side of the support sheet 2 of the film chip 1. The suction cup 70a is supported on a base portion which is moved back and forth and up and down by a drive mechanism (not shown) and is connected to a suction pump (not shown) through a vacuum tube. The suction pad 70 takes out the film chip 1 from the cartridge 20 in the manner described above and transfers the film chip 1 to the position where the sample liquid is applied on the film chip 1.

As shown in FIG. 8, the transfer member 73 is like a horseshoe in shape and has a flat upper surface. That is, the transfer member 73 is bifurcated in the front end portion to form a pair of arm portions 73b extending on opposite sides of a cutaway portion 73a, and a plurality of suction holes 74 are formed to surround the cutaway portion 73a and to open in the upper surface of the transfer member 73. The suction holes 74 are connected to a suction pump (not shown) through a vacuum tube 75. The base portion 73c of the transfer member 73 is connected to a drive mechanism (not shown) to be inserted into the cell 42 in the incubator 12 through the side opening 42a of the incubator 42.

When the transfer member 73 receives the film chip 1 from the suction pad 70, the transfer member 73 is moved toward the suction pad 70 holding the film chip 1 and is stopped in a position where the suction pad 70 is in the cutaway portion 73a of the transfer member 73 with the film chip 1 positioned above the cutaway portion 73a. Then the suction pad 70 is moved downward below the transfer member 73 leaving the film chip 1 on the transfer member 73. The film chip 1 left on the transfer member 73 is held thereon under the suction force provided through the suction holes 74. When the position of the suction pad 70 relative to the film chip 1 held thereby is accurately controlled, the position of the transfer member 73 relative to the film chip 1 can be accurately controlled and a predetermined amount of the sample liquid can be accurately applied to the center of the reagent layer 3 of the film chip 1 held by the transfer member 73.

The suction member 76 is positioned below the cell 42 in the incubator 12 and comprises a suction cup supported on a base portion (not shown) to be moved up and down by a drive mechanism not shown) into and away from the cell 42 through the light measuring window. The suction cup is connected to a suction pump (not shown) through a vacuum hose.

A film takeout means 17 is disposed in the film takeout position of the incubator 12. The film takeout means 17 comprises a takeout suction pad 81 which attracts the film chip 1 in the cell 42 which has finished with measurement and lifts it, a horseshoe-like transfer member 82 which receives the film chip 1 from the takeout suction pad 81 and transfers it outside the incubator 12 and a discarding suction pad 83 which receives the film chip 1 from the transfer pad 82 and discards it into a discarding box 84.

The sample liquid supplier 14 comprises a turn table 85 which is rotated by a drive mechanism 86. The turn table 85 holds a plurality of sample tubes 87 filled with sample liquids which are arranged along the circumferential edge of the turn table 85 and is rotated to bring the sample tubes 87 to a sample liquid supplying position one by one. A plurality of nozzle tips 88 which are mounted on a spotting nozzle 91 to be described later are held on the turn table 85 inside the sample tubes 87.

The spotting means 15 for applying the sample liquid to the film chip 1 comprises a spotting nozzle 91 which sucks and discharges the sample liquid, and a nozzle tip 88 like a pipette is demountably mounted on the nozzle 91. The nozzle 91 is moved up and down and rotated by a drive mechanism 92. That is, the nozzle 91 sucks the sample liquid from the sample liquid supplier 14, is moved to the film chip 1 held by the transfer member 73, and then applies the sample liquid to the film chip 1. The nozzle tip 88 is changed every time the sample liquid is changed.

The film chip 1 applied with the sample liquid is transferred to the incubator 12 and incubated there. After incubation for a predetermined time, the optical density of the reagent layer 3 is measured by the light measuring system 16 disposed below the incubator 12. The light measuring system 16 comprises said light measuring head 95 for measuring the optical density of the color formed by the coloring reaction between the reagent layer 3 and the sample liquid. The light measuring head 95 projects measuring light containing light of a predetermined wavelength onto the reagent layer 3 through the support sheet 2 and detects reflected light with a photodetector. Light from a light source (lamp) 96 enters the light measuring head 95 through a filter 97 and is caused to impinge upon the reagent layer 3 by the head 95. A plurality of kinds of the filters 97 are mounted on a rotary disk 98 which is driven by an electric motor 99 and one of the filters 97 is selected according to the item of measurement.

The reflected light from the reagent layer 3 carries thereon optical information (more particularly the amount of light) on the amount of coloring matter formed by the coloring reaction between the reagent layer 3 and the sample liquid. The reflected light is received by the photodetector and the optical information carried by the reflected light is converted to an electric signal by the photodetector. The electric signal is input into a determination section through an amplifier. The determination section determines the optical density of the coloring matter formed by the coloring reaction between the reagent layer 3 and the sample liquid on the basis of the level of the electric signal and determines the concentration of a predetermined chemical component in the sample liquid.

The measurement by the biochemical analysis system 10 is effected in the following manner. That is, a film chip 1 is taken out by the suction pad 70 of the transfer means 13 from a cartridge 20 storing therein chemical analysis film chips 1 corresponding to the item of measurement. The film chip 1 held by the suction pad 70 is transferred to the transfer member 73 with the reagent layer 3 facing upward and a sample liquid is applied to the reagent layer 3.

That is, a nozzle tip 88 is mounted on the spotting nozzle 91 of the spotting means 15 and the spotting nozzle 91 is moved above a desired sample tube 87 in the sample liquid supplier 14. Then the nozzle 91 is moved downward to bring the nozzle tip 88 into the sample liquid and the nozzle 91 sucks a predetermined amount of the sample liquid into the nozzle tip 88. Thereafter the nozzle 91 is moved above the center of the film chip 1 on the transfer member 73 and moved downward toward the film chip 1, where a predetermined amount of sample liquid is applied to the reagent layer 3 from the nozzle tip 88. The sample liquid spreads over the reagent layer 3 and mixes with the reagent therein.

The film chip 1 applied with the sample liquid is inserted into one of the cells 42 of the incubator 12 through the side opening 42a by the transfer member 73.

Coloring reaction (coloring matter forming reaction) is caused when the film chip 1 with the sample liquid is heated to a predetermined temperature in the cell 42 in the incubator 12, and the optical density of the coloring matter is measured by the light measuring head 95 after a predetermined time or at predetermined intervals.

When the suction pad 70 takes out the film chip 1 from the cartridge 20, it is preferred that the cartridge 20 is precisely positioned with respect to the suction pad 70 (a film takeout means) so that the suction pad 70 can precisely attract a predetermined portion of the film chip 1a.

A method of and a device for precisely positioning the cartridge 20 with respect to the suction pad 70 (a film takeout means) so that the suction pad 70 can precisely attract a predetermined portion of the film chip 1a will be described with reference to FIGS. 10 to 18, hereinbelow.

Figure 10:
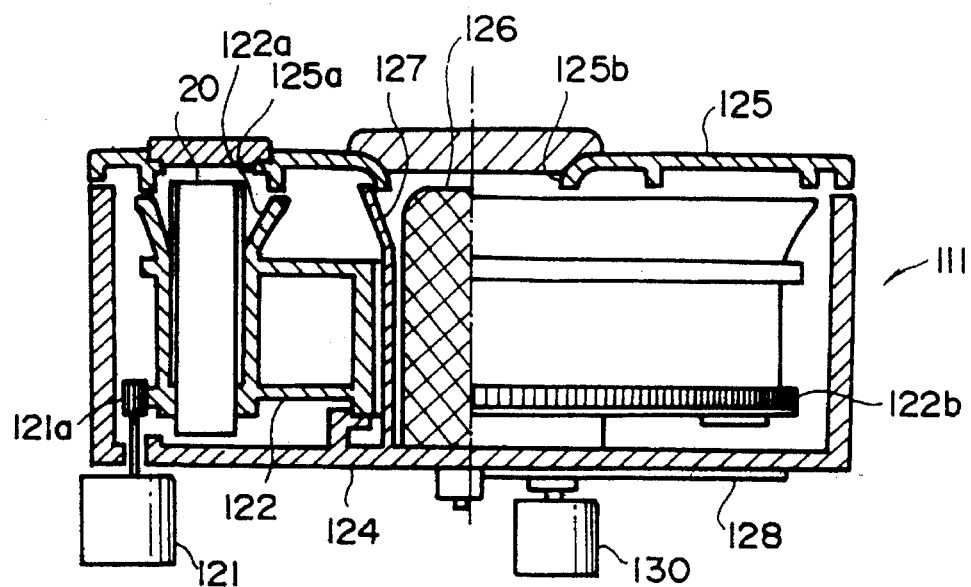
FIG. 10 is a schematic cross-sectional view showing a film supplier employed in carrying out the method of positioning the cartridge in accordance with the present invention.
Figure 11:
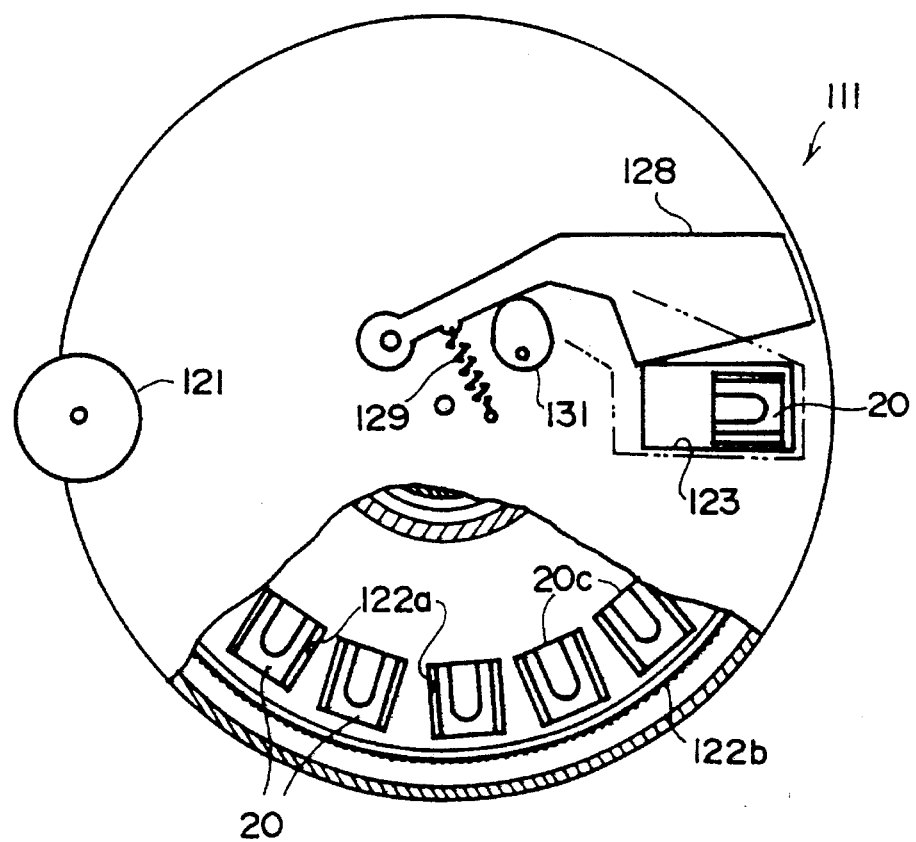
FIG. 11 is a bottom view partly cut away of the film supplier shown in FIG. 10.
Figure 12:
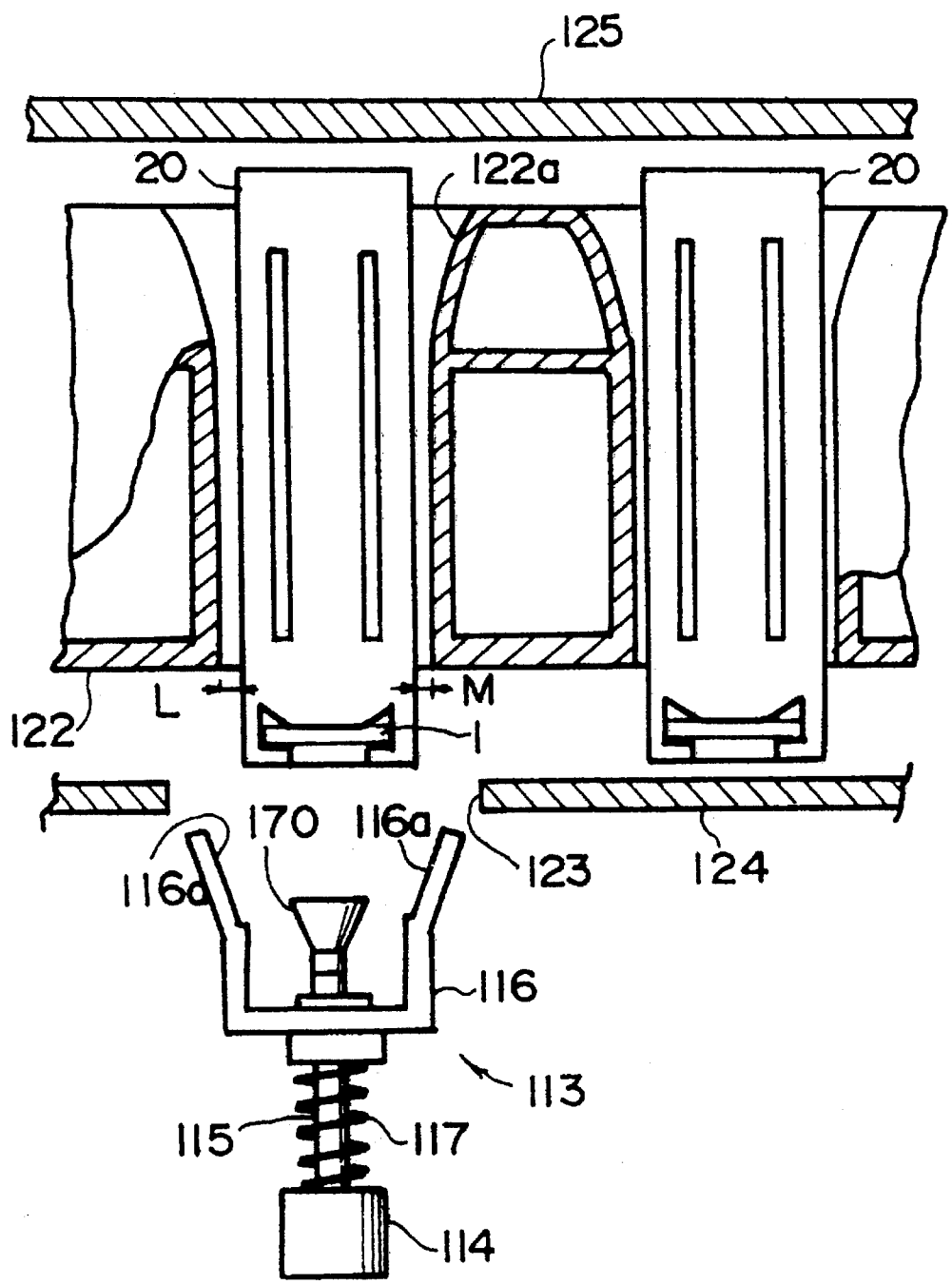
FIG. 12 is a fragmentary view showing an important part of a film takeout device in accordance with an embodiment of the present invention.

FIG. 10 is a cross-sectional view showing a film supplier 111 which is suitable for carrying out the method of the present invention, FIG. 11 is a bottom view partly cutaway of he film supplier 111 and FIG. 12 is a fragmentary view showing a device for positioning the cartridge 20 in accordance with an embodiment of the present invention.

The film supplier 111 is basically the same as the film supplier 11 shown in FIG. 6. That is, the film supplier 111 is provided with disk-like support 122 which is supported for rotation on a base portion 124. The support 122 has a plurality of cartridge holding portions 122a which are arranged in inner and outer circles on the support 122 and a plurality of cartridges 20 loaded with the film chips 1 are held in the respective cartridge holding portions 122a.

The support 122 is provided with a cover 125 which tightly encloses the inner space of the film supplier 111. The cover 125 is provided with a pair of openings 125a provided with lids and the cartridges 20 can be taken out and inserted into the cartridge holding portion 122a through the openings 125a. The cover 125 can be removed from the base portion 124, and in the case where trouble occurs in the film supplier 111 and the cartridges 20 are to be transferred to other place, the cover 125 is removed from the base portion 124 so that the cartridges 20 can be taken out quickly. An dehumidifying agent holding portion 127 is formed in the support 122 at the center thereof and dehumidifying agent (dessicant) 126 is loaded in the dehumidifying agent holding portion 127 through an opening 125b formed in the cover 125 at the center thereof. The opening 125b is provided with a lid. Thus the inner space of the film supplier 11 is kept dry. A film takeout port 123 for taking out a predetermined film chip 1 from the cartridge 20 and a shutter 128 for opening and closing the port 123 are formed in the bottom wall of the base portion 124. The shutter 128 is urged by a spring 129 toward a closing position in which it closes the port 123 and is driven to an open position where it opens the port 123 by a cam 131 which is rotated by a shutter motor 130.

Teeth 122b are formed on the peripheral surface of the support 122 and are in mesh with a gear 121a fixed to the output shaft of a support motor 121. The support 122 is rotated by the support motor 121 so that a predetermined one of the cartridge holding portions 122a is brought to a film takeout position opposed to the film takeout port 123. As shown in FIG. 12, a film takeout means 123 is provided below the film takeout port 123 to take out the chemical analysis film chip 1 from the cartridge 20 in the film takeout position.

The structure of the film takeout means 113 and the method of taking out the chemical analysis film chip 1 from the cartridge 20 will be described, hereinbelow. FIGS. 13A to 13D show the procedure for taking out the film chip 1 by the film takeout means 113 shown in FIG. 12.

As shown in FIG. 12, the film takeout means 113 comprises a base portion 114, a suction pipe 115 mounted on the base portion 114, a suction pad 170 connected to the suction pipe 115, a guide member 116 mounted on the suction pipe 115 to be movable up and down relative to the suction pipe 115, and a drive mechanism not shown. A coil spring 117 is provided on the suction pipe 115 between the guide member 116 and the base portion 114, and the suction pipe 115 is connected to a suction pump (not shown) through the base portion 114.

The cartridge 20 is held in each cartridge holding portion 122a with a predetermined play. That is, the inner size of the cartridge holding portion 122a as measured in the circumferential direction of the support 122 is larger than the outer size of the cartridge 20 as measured in the circumferential direction of the support 122 by a predetermined length (i.e., the sum of L and M in FIG. 12) and the inner size of the cartridge holding portion 122a as measured in the radial direction of the support 122 is substantially equal to the outer size of the cartridge 20 as measured in the radial direction of the support 122. Accordingly, the cartridge 20 is permitted to move in the cartridge holding portion 122a in the circumferential direction of the support 122 by a limited distance while it cannot move in the radial direction.

When a cartridge 20 is brought to the film takeout position opposed to the film takeout port 123 by rotation of the support 122, the position of the cartridge 20 in the circumferential direction of the support 122 slightly varies due to error in precision of the support drive mechanism. The position of the film takeout means 113 relative to the film takeout port 123 can be set with a high accuracy. More particularly, the film takeout means 113 is set in such a position that when the suction pad 170 is moved right upward from the position, it can be precisely brought into contact with the lowermost film chip 1 in the cartridge 20 at the center of the film chip 1 so long as the cartridge 20 is precisely positioned in a predetermined calculative position relative to the film takeout port 123.

The guide member 116 has a pair of wall portions which extend substantially vertically spaced from each other in the direction of the width of the cartridge 20 (in the circumferential direction of the support 122). The wall portions are bent outward at intermediate portions so that the space therebetween increases toward the upper ends thereof, whereby a pair of inclined guide surfaces 116a are formed. The space between the guide surfaces 116a at the top ends thereof are sufficiently larger than the width of the bottom of the cartridge 20 so that the bottom of the cartridge 20 can be successfully received between the guide surfaces 116a even if the position of the cartridge 20 is shifted from said calculative position within said play. On the other hand, the space between the guide surfaces 116a at the base of the inclined guide surfaces 116a are substantially equal to the width of the bottom of the cartridge 20.

When a desired cartridge 20 is stopped in the film takeout position opposed to the film takeout port 123 and the film takeout port 123 is opened, the film takeout means 113 is moved right upward into the film supplier 111 through the film takeout port 123 as shown in FIG. 13A. When the cartridge 20 is in a position shifted from the calculative position, one edge of the bottom of the cartridge 20 is brought into abutment against one of the guide surfaces 116a as the film takeout means 113 moves upward and as the film takeout means 113 moves further upward, the edge of the bottom of the cartridge 20 slides along the guide surface 116a and the cartridge 20 is pushed toward the calculative position due to inclination of the guide surface 116a. In this manner, by the time when the bottom of the cartridge 20 is received between the bases of the inclined guide surfaces 116a, the cartridge 20 can be precisely positioned in the calculative position as shown in FIG. 13B.

Then the suction pad 170 is inserted into the cartridge 20 through the second opening 20e and brought into a close contact with the lowermost film chip 1 in the cartridge 20. The suction pad 170 holds the lowermost film chip 1 under a suction force and slides it radially inwardly as shown in FIG. 13C. In this manner, the film takeout means 113 takes out the chemical analysis film chip 1 from the cartridge 20 as shown in FIG. 13D.

The cartridge, the method of taking out the chemical analysis film chip 1 from the cartridge, and method of and device for positioning the cartridge with respect to the suction means in accordance with the present invention need not be limited to those described above but may be variously modified.

For example, though in the embodiment described above both the spaces c between the respective edges 20i of the second opening 20e and the upper edge of 20j of the first opening 20c just above the edges 20i are strictly set to a value larger than the thickness of one film chip 1 and smaller than double the thickness of the same, substantially the same effect can be obtained by setting only one of the spaces c to such a value and setting the width of the first opening 20c' to a larger value as shown in FIG. 9.

Further instead of urging downward the stack of the film chips 1 by the spring member 30, the stack may be urged by a ratchet mechanism or if the film chips 1 can be surely caused to fall toward the second opening 20e by their own weights, such an urging means may be eliminated.

Further the shape of the protrusion 201 projecting into the first opening 20c need not be limited to that described above in conjunction with FIGS. 4A and 4B but may be of various shapes so long as the protrusion permits the reshaped film chip 1 to pass through the first opening 20c while preventing the chemical analysis film chip 1 in the normal state from passing therethrough.

Further though in the embodiment described above, the film chips 1 are taken out with the cartridge 20 positioned so that the second opening 20e opens downward, the film chips 1 may be taken out with the cartridge 20 positioned inversely.

Further, though, in the above embodiment, the film chip comprises three layers, the support sheet, the reagent layer and the spreading layer, the film chip may comprise a support sheet and a reagent-containing porous layer.

Further the automatic biochemical analysis system for carrying out biochemical analysis using the chemical analysis film chip of the present invention need not be limited to that described above but may be variously modified so long as it can carry out biochemical analysis with a high accuracy without damaging the film chip.

Further, though in the embodiment described above, the guide member 116 is arranged to be brought into a sliding engagement with the edges of the bottom of the cartridge 20, the guide member 116 may be in the form of a tapered member having an inclined guide surfaces 116a which are inserted between the ribs 20h on the cartridge 20 to be brought into a sliding engagement therewith as shown in FIGS. 14A to 14C.

Figure 15A:
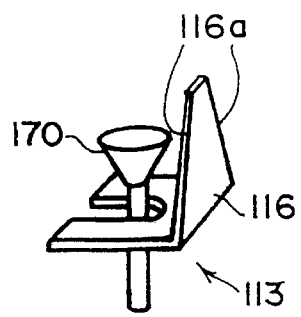
Figure 15B:
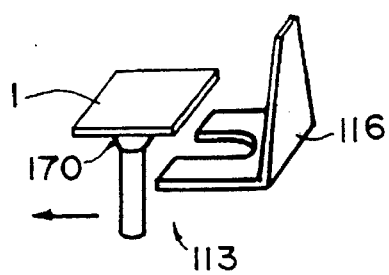
Figure 16:
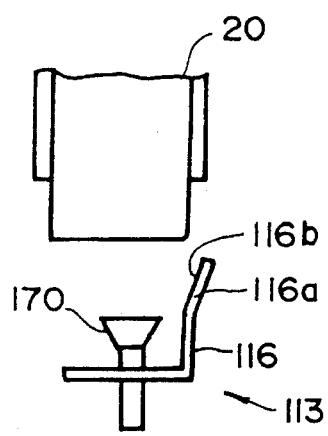
FIG. 16 is a perspective view showing another modification of the film takeout device shown in FIG. 10.

Further, though in the embodiment described above and the modification shown in FIGS. 14A to 14C, the guide member 116 is integral with the suction pad 170, the guide member 116 may be movable independent from the suction pad 170 as shown in FIGS. 15A and 15B. In this case, though it is preferred that the guide member 116 be moved upward to correct the position of the cartridge 20 in synchronization with the suction pad 170, it may be moved upward to correct the position of the cartridge 20 in response to, for instance, movement of the shutter 128 before upward movement of the suction pad 170.

Though, in the embodiment described above, the position of the cartridge 20 is corrected only in the circumferential direction of the support 122, if necessary, it is possible to correct the position of the cartridge 20 also in the radial direction of the support 122 by providing a play in the radial direction between the cartridge holding portion 122a and the cartridge 20. In this case, for example, the upper portion of the guide member 116 shown in FIGS. 14A to 14C is inclined to form an inclined guide surface 116b so that the guide surface 116b is brought into a sliding engagement with the radially inner edge of the bottom of the cartridge 20 as the suction pad 170 is moved upward.

Figure 17:
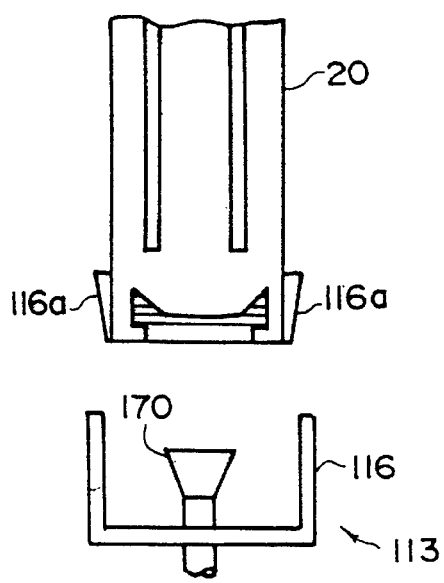
FIG. 17 is an example where the guide surfaces are provided on the cartridge.

Further, though, in the embodiment described above, the guide surfaces 116a are provided on the guide member 116, the guide surfaces 116a may be provided on the cartridge 20 as shown in FIG. 17.

Figure 18:
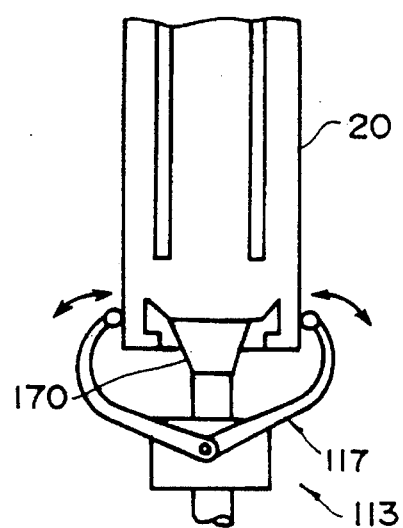
FIG. 18 is a schematic view showing another example of the film takeout device.

Further the position of the cartridge 20 may be corrected by use of a mechanism 117 such as shown in FIG. 18 instead of correcting the position of the cartridge 20 by sliding engagement between the cartridge 20 and the guide member 116.

In the embodiment described above, it is important that the cartridges 20 are held in the cartridge holding portions 122a with the first opening 20c directed radially inwardly of the support 122 so that the film chip 1 can be taken out by sliding the film chip 1 radially inwardly as clearly shown in FIG. 11. If the cartridges 20 are held in the cartridge holding portions 122a with the first opening 20c directed radially outwardly of the support 122 so that the film chip 1 is taken out by sliding it radially outwardly, the cartridge holding portions 122a must be positioned inwardly away from the peripheral edge of the support 122 so that a space for taking out the film chip 1 is formed between the peripheral edge of the support 122 and the cartridge holding portions 122a, which reduces the number of the cartridges 20 to be accommodated in the film supplier 111 of a given size.

In the conventional system where the chemical slides having a frame are used, the slides are taken out from the cartridge by a pushing mechanism which pushes out the slide. However such a pushing mechanism is difficult to apply when the cartridge holding portions are arranged in a circle, especially in a plurality of concentric circles as in the film supplier 11 shown in FIG. 1. Further since the pushing mechanism is generally disposed at the center of the film supplier, the dehumidifying agent (dessicant) cannot be disposed at the center of the film supplier but can be disposed only in a peripheral portion of the film supplier. Further the dehumidifying agent is loaded and unloaded only from below the film supplier. By using the suction pad 70 or 170 to take out the film chip 1, such drawbacks can be eliminated.

What is claimed:

1. A device for taking out a film chip from a cartridge held by a cartridge holding means, said device comprising: a suction means for attracting the film chip under a suction force in a predetermined attracting position, wherein said cartridge holding means is arranged to hold the cartridge with a predetermined play in at least one direction, and there is provided a guide means associated with the suction means for engaging the cartridge held by the cartridge holding means to guide the cartridge in the vicinity of the suction means to a predetermined conforming position, said predetermined conforming position being a position where the cartridge is to be positioned with respect to the suction means in order to permit the suction means to precisely attract a predetermined portion of the film chip.

2. A device as defined in claim 1 in which the guide means guides the cartridge to the conforming position in response to movement of the suction means to the attracting position.

3. A device as defined in claim 1 in which the guide means comprises a guide member which slidably engages a portion of the cartridge to guide the cartridge to the conforming position when the guide means is moved toward the cartridge which is held by the cartridge holding means.

4. A device as defined in claim 1 in which the guide means is slidably engaged with at least one bottom edge of the cartridge.

5. A device as defined in claim 1 in which the guide means is slidably engaged with at least one rib formed on the cartridge.

6. A device as defined in claim 1 in which the guide means is integral with the suction means.

7. A device as defined in claim 1 in which the guide means is disposed so as to be movable independently of the suction means.

8. A device as defined in claim 1 in which the cartridge holding means is a disk shaped support having a plurality of cartridge holding portions arranged around the support, and in which a plurality of cartridges, each one of the cartridges being held in a respective one of the holding portions, are provided.

9. A device as defined in claim 8 in which the at least one direction is a circumferential direction of the support.

10. A device as defined in claim 8 in which the at least one direction is a radial direction of the support.

11. A device as defined in claim 3 in which the guide member comprises inclined guide surfaces for guiding the cartridge to the predetermined conforming position.

12. A device as defined in claim 1 in which inclined guide surfaces are provided on a lower portion of the cartridge, the inclined guide surfaces contacting the guide means for guiding the cartridge to the predetermined conforming position.

* * * * *